US007348417B2

(12) United States Patent
Sorokin et al.

(10) Patent No.: US 7,348,417 B2
(45) Date of Patent: Mar. 25, 2008

(54) METHOD OF PURIFYING MOXIDECTIN THROUGH CRYSTALLIZATION

(75) Inventors: Isidoro H. Sorokin, La Plata (AR); Paola Di Raimondo, Catania (IT); Chin-Liang Chou, Audubon, PA (US)

(73) Assignee: Wyeth, Madison, NJ (US)

( * ) Notice: Subject to any disclaimer, the term of this patent is extended or adjusted under 35 U.S.C. 154(b) by 344 days.

(21) Appl. No.: 10/894,965

(22) Filed: Jul. 20, 2004

(65) Prior Publication Data

US 2005/0033041 A1 Feb. 10, 2005

Related U.S. Application Data

(60) Provisional application No. 60/493,317, filed on Aug. 7, 2003.

(51) Int. Cl.
*C07H 1/06* (2006.01)
*C07H 17/08* (2006.01)

(52) U.S. Cl. ....................................... 536/7.1; 536/127

(58) Field of Classification Search ................. 536/7.1, 536/127
See application file for complete search history.

(56) References Cited

U.S. PATENT DOCUMENTS

| | | | |
|---|---|---|---|
| 4,916,154 | A | 4/1990 | Asato et al. |
| 4,988,824 | A | 1/1991 | Maulding et al. |
| 5,106,994 | A | 4/1992 | Carter et al. |
| 5,169,956 | A | 12/1992 | Carter et al. |
| 5,198,464 | A | 3/1993 | Wood et al. |
| 5,317,030 | A | 5/1994 | Wood et al. |
| 5,418,168 | A | 5/1995 | Carter |
| 5,439,934 | A | 8/1995 | Wood |

*Primary Examiner*—Elli Peselev
(74) *Attorney, Agent, or Firm*—Gloria K. Szakiel

(57) ABSTRACT

Methods for the purification of the macrolide moxidectin result in higher purity levels than can often otherwise be obtained. The crystalline moxidectin is then used in a wide variety of pharmaceutical and veterinary applications, including the prevention, treatment and control of parasites in plants, animals and humans.

24 Claims, No Drawings

METHOD OF PURIFYING MOXIDECTIN THROUGH CRYSTALLIZATION

This application claims the benefit under 35 U.S.C. §119 (e) to U.S. provisional application No. 60/493,317 filed Aug. 7, 2003, which is hereby incorporated by reference in its entirety.

FIELD OF THE INVENTION

The present invention relates generally to the purification of chemical compounds with pharmacological properties and veterinarian uses. More specifically, the invention relates to novel methods of purifying moxidectin, and to the moxidectin obtained thereby.

BACKGROUND OF THE INVENTION

The present invention relates to the purification of the anthelmintic compound known as moxidectin. The chemical name for moxidectin is [6R,23E,25S(E)]-5-O-Dementhyl-28-deoxy-25-(1,3-dimethyl-11-butenyl0-6,28-epoxy-23-9methoxyimino)milbemycin B. The composition of moxidectin and various uses thereof are described in U.S. Pat. No. 4,916,154, Asato, et. al, and in U.S. Pat. No. 4,900,753, Sutherland, et. al. The morphological characteristics, compounds and methods of production for moxidectin are further disclosed in U.S. Pat. No. 5,106,994, and in its issued European counterpart, EP 170,006. Another process used to purify moxidectin is disclosed in U.S. Pat. No. 4,988,824.

Moxidectin is useful as an anti-parasitic in the prevention, treatment or control of helmintic, ectoparasitic, insect, acarid and nematode infections and infestations in warm-blooded animals, as well as agricultural crops. It is especially useful to cattle and sheep farmers to control such parasites as ticks and worms. Moxidectin may be administered to livestock and other animals in a number of ways including, as a topical or "drench", as a subcutaneous injection, or orally in pill or tablet form.

Two methods currently used to purify moxidectin are described as examples 17 and 19 of U.S. Pat. No. 4,988,824. The methods of examples 17 and 19 yield purity levels of 89% and 71%, respectively. Another process currently known and used to purify moxidectin involves the following steps: dissolving moxidectin in cyclomethylhexane, (MCH), and adding water to the moxidectin/MCH solution resulting in the precipitation of moxidectin over an extended period of time. The process results in a product with 90-92% purity, but can take days to complete. The current methods are cost-intensive, time-consuming and result in an end product with a purity level that is not high enough for many applications.

A higher purity level would further enable suitable formulations of pharmaceutical preparations for animal, as well as human uses. A method that would allow for amorphous moxidectin to be converted to crystalline moxidectin with a higher purity would also be useful to the skilled artisan.

Other methods of moxidectin currently available to the skilled artisan may achieve a higher purity level, but typically will utilize more hazardous solvents such as chloroform and dichloromethane. They also can involve more complicated processes such as normal and reverse chromatography steps (silica media).

Therefore, what is needed in the art is a new method to purify moxidectin that is cost-effective, less time consuming, and produces an end product with a higher purity level than is currently available. Also needed is moxidectin with a higher purity level than what is otherwise available in the art that is safe for use in a wide variety of pharmaceutical applications, including those for animal and even human uses.

SUMMARY OF THE INVENTION

In one embodiment of the invention there is provided a method for purifying moxidectin which comprises combining moxidectin with a first solvent to produce a moxidectin solution. The solution is then concentrated at a temperature at or below about 50° C., and thereafter the temperature of the moxidectin solution is cooled to a temperature within the range of about 40° to 30° C. A second solvent is combined with the moxidectin solution; and thereafter the moxidectin solution is agitated while lowering the temperature to within the range of about 30 to 10° C., so as to generate moxidectin crystals from the solution. The crystals from the moxidectin solution are then purified, and dried.

In a further embodiment, the method to purify solid moxidectin involves dissolving solid moxidectin in methylcyclohexane, (MCH), thereby resulting in a moxidectin/MCH solution. Next, the moxidectin/MCH solution is concentrated at a pot temperature of about 45° C. to 50° C. under vacuum. N-heptane is added to the moxidectin/MCH solution, at a ratio of about 1:4 MCH to n-heptane, under agitation. The resultant solution is then aged for about 4-5 hours at about 30° C., and thereafter the solution is further aged at a temperature of about 10° C. for about 2-3 hours so as to generate moxidectin crystals. The resultant crystalline moxidectin so obtained is filtered and dried under vacuum.

The invention also provides a process for generating moxidectin crystals from amorphous moxidectin. According to this embodiment, amorphous moxidectin is first added to a first solvent to produce a moxidectin solution. Next, using distillation, the weight percentage of moxidectin within the solution is caused to be within the range of about 40-44% at a temperature within the range of about 45-50° C. for the solution. The solution is then cooled, and a second solvent is added to the moxidectin solution at a temperature within the range of about 30-35° C. for the solution. The temperature of the solution is next lowered to about 10° C. over the period of about 2-8 hours, while agitating the solution such that the agitation increases over the time period above so as to effect crystallization of the moxidectin. The moxidectin crystals are then dried and recovered.

The invention also provides moxidectin crystals purified according to the various embodiments herein described which are about 94-96%, or higher, pure, and are described as substantially solvent-free and suitable for a wide range of pharmaceutical applications, including those in the veterinary and human fields.

In addition, the invention provides compositions of moxidectin using the crystalline moxidectin herein obtained in a large range of suitably effective anthelmintic and anti-parasitic applications.

These and other objects of the invention will become more apparent from the detailed description of the invention provided hereinbelow.

DETAILED DESCRIPTION OF THE INVENTION

Moxidectin in its crystalline form can be conveniently incorporated into many veterinarian pharmaceutical formulations. These veterinarian formulations are useful as anthelmintics, ectoparasiticides, insecticides, acaricides and nematicides,—for preventing and controlling diseases in warm-blooded animals, such as poultry, cattle, sheep, swine, rabbits, horses, dogs, cats and human beings and agricultural crops. Moxidectin is suitable for incorporation into topical, oral, subcutaneous and various other veterinarian and pharmaceutical formulations. The pharmaceutical and veterinarian formulations may be administered in a variety of ways including: injectable and sustained release formulations, solutions, suspensions, bolus, oral tablets and liquid drenches for use as an anthelmintic for animals.

The present invention involves making a solution of moxidectin and a first solvent. The moxidectin may be obtained from whatever source is available to the skilled artisan. Preferably, the moxidectin is in its unpurified or "raw", or amorphous form. It may be derived from a small- or large-scale (industrial) process typically utilized for producing moxidectin. The moxidectin may be obtained from a deblocking chemical reaction, such as by alkaline hydrolysis. By way of non-limiting example, the process described in U.S. Pat. No. 4,988,824 is a useful method for generating moxidectin. Typically, the moxidectin useful in the process hereinafter described will have an initial purity (dried) of less than about 92%, many times within the range of about 90-92%.

The first solvent is preferably selected from the group consisting of methanol, ethanol, methylcyclohexane, hexane, benzyl alcohol, toluene, heptane, and mixtures thereof. Other solvents capable of dissolving moxidectin may also be utilized. Cost and safety profiles will further affect the selection of a suitable solvent. Most preferred solvents will be physiologically tolerated in very trace amounts and thus will be suitable for inclusion in trace amounts in pharmaceutical preparations. Of these, preferably cyclomethylhexane (MCH), is used as the first solvent. The moxidectin is combined with the first solvent in a weight ratio within the range of about 1:1 to 1:2 to produce the moxidectin solution.

After the moxidectin and first solvent are combined, the resultant moxidectin solution is then concentrated, preferably under vacuum. As a result of this concentrating step, the percentage of the moxidectin in the moxidectin solution is made to be about 40-50% by weight, and preferably about 40-44% by weight. Concentration of the moxidectin in the solution is typically effected at a temperature at or below about 50° C., with a temperature within the range of about 40-50° C. being preferred, and a temperature within the range of about 45-50° C. being especially desirable. Distillation, using accepted protocol, is the preferred means of obtaining the desirable moxidectin concentration. In yet another embodiment, the moxidectin/first solvent (e.g., MCH) solution is distilled under vacuum at a pot temperature of about 45° to 50° C. The use of a vacuum and control of the temperature range are used to minimize thermal effects such as compound degradation.

Thereafter, the temperature of the concentrated moxidectin solution is cooled and regulated to approximately 30° C., and may vary within a range of about 30-40° C.

Next, a second solvent is added to the moxidectin solution. This second solvent is preferably a non-polar organic solvent. Even more desirably, the second solvent is selected from the group consisting of hexane, heptane, toluene, isooctane, other non polar organic solvents capable of dissolving moxidectin or mixtures thereof. Of these, n-hexane and n-heptane are often particularly preferred. Other suitable non polar organic solvent may be selected by those skilled in the art, and can be ascertained by evaluation of physical and chemical properties of the molecular species to be crystallized. Cost and safety profiles will often affect the selection of a suitable non polar organic solvent as well. Most preferred non polar organic solvents will be physiologically tolerated in very trace amounts and thus will be suitable for inclusion in trace amounts in pharmaceutical preparations.

The second solvent is added in a weight ratio with respect to the first solvent within a range of about 2:1 to 6:1. It is more preferably that this weight ratio be about 3:1. Preferably, the second solvent is added under agitation, such as by stirring.

More hazardous solvents such as chloroform and dichloromethane, are preferably avoided as part of the method of the invention.

After adding the second solvent; the moxidectin solution is further regulated to a temperature between about 30° C.-10° C.; and even more preferably between about 25-10° C. Even more desirably, the temperature of the solution is gradually lowered from the high end to the low end of the ranges just described, preferably under agitation, as by gentle stirring. This part of the process of the invention will generate moxidectin crystals from the solution. Preferably, a time period of about 2 to 12 hours, more preferably about 3 to 6 hours is utilized to effect optimal crystalline formation. This in itself is an advance over the state of the art, in which it was often necessary to devote up to 48 hours or more for crystallization.

Thereafter, the moxidectin crystals are filtered from the solution. This can also be achieved under gentle agitation. Once obtained, the moxidectin crystals are dried, preferably under vacuum. The dried moxidectin crystals should desirably be substantially solvent-free, that is, they should contain at most only trace amounts of residual solvent within established pharmaceutical standards.

The resulting moxidectin crystals obtained according to the purification method of the invention will typically have a purity level within the range of about 94%-96%, which is higher than a beginning purity level of 90%-92% often obtained as a result of making amorphous moxidectin using known synthesis protocol. In any event, the invention contemplates an ending purity level which is about 1.5 to 10% or greater, more preferably about 2 to 6%, higher than the starting level of purity for the moxidectin. Purity levels may be measured by high pressure liquid chromatography, (HPLC) using accepted protocol. Other methods available in the art for measuring purity may also be utilized.

The moxidectin crystals of the invention may be utilized in a wide variety of pharmaceutical applications, especially veterinarian products. Thus, the moxidectin obtained according to the process hereinabove described may be incorporated into several anti-parasitic, endectoside and anthelmintic products, as well as other related applications.

If desired, the method of the invention may be repeated one or more additional times to optimize purity, if desired.

The following example illustrates one or more preferred aspects of the invention and is provided by way of illustration only, and should not be construed as limiting the scope thereof.

EXAMPLE 1

Table One reports purification results obtained by the procedure of the invention, while varying different aspects of the process.

TABLE 1

| MTM Solids Used (Grams) | MCH Used (Grams) | Initial Purity of MTM Used | TS Conc. % after MCH Distillation | Solvent Used | Weight Ratio of solvent to MCH | Crystallization Temperature ° C. | Purity % MTM (after Isolation)* |
|---|---|---|---|---|---|---|---|
| 5 | 7.7 | 92.6% | 39.0% | n-Hexane | 3:1 | Room Temperature (RT) | 94.0% |
| 5 | 7.5 | 93.1% | 40.0% | n-Hexane | 3:1 | (RT) | 96.3% |
| 5 | 7.5 | 93.1% | 40.0% | n-Hexane | 4:1 | (RT) | 94.2% |
| 5 | 7.5 | 93.1% | 40.0% | n-Hexane | 5:1 | (RT) | 94.5% |
| 16.2 | 24.28 | 93.8% | 40.0% | n-Heptane | 3:1 | 10° C. | 96.1% |
| 19.8 | 29.73 | 93.8% | 40.0% | n-Heptane | 3:1 | 25° C. | 95.0% |
| 9.9 | 14.91 | 93.0% | 40.0% | n-Heptane | 3:1 | 25° C. | 95.6% |

*(Purity % MTM (Moxidectin Technical Material) after Isolation is solvent-free purity)
TS = Total Solids The present invention imparts the several advantages over the currently used methods of moxidectin purification, as exemplified in the U.S. Pat. No. 4,988,824 in examples 17 and 19. The present invention can be accomplished in a matter of hours, whereas the currently used methods may take days to complete. The present invention produces a crystalline moxidectin product with a purity level of approximately 94% to 96%, whereas the currently used methods result in an end product with a purity level of less than 92%. Additionally, the present invention results in a cost savings in comparison to the currently used methods.

A further advantage of the current invention pertains to batch production. Utilization of the current invention allows for recovery of moxidectin that is not pure enough to meet defined specification standards or has decomposed. Recovery can be accomplished by simply repeating the crystallization process, thus increasing the purity level of the moxidectin to meet the defined specification standards, while saving a batch that would have otherwise been wasted.

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A method for purifying moxidectin, said method comprising:
   a) combining moxidectin with a first solvent to produce a moxidectin solution wherein said first solvent is methylcyclohexane;
   b) concentrating said solution at a temperature at or below about 50° C., and thereafter cooling the temperature of said moxidectin solution to a temperature within the range of about 40° to 30° C.;
   c) combining a second solvent with said moxidectin solution wherein said second solvent is selected from hexane, heptane, toluene, isooctane or a mixture thereof and is present in a weight ratio of 2:1 to 6:1 of second solvent to first solvent; and thereafter
   d) agitating the moxidectin solution while lowering the temperature to within the range of about 30 to 10° C., so as to generate moxidectin crystals from said solution;
   e) filtering said crystals from said moxidectin solution; and
   f) drying said crystals.

2. The method of claim 1 wherein said dried crystals have a purity of least about 94%.

3. The method of claim 1 wherein said dried crystals have a purity of about 94-96%.

4. The method of claim 1 wherein the moxidectin solution has a total solids concentration range of about 40-50%.

5. The method of claim 4 wherein the moxidectin solution has a total solids concentration range of about 40-44%.

6. The method of claim 1 wherein said second solvent is added under agitation.

7. The method of claim 6 wherein agitation of said moxidectin solution is performed at a rate of 15-30 rpm while said second solvent is added; and thereafter the agitation rate of said moxidectin solution is increased to a rate of 50-70 rpm.

8. The method of claim 1 wherein part d) said temperature is lowered from about 25 to 10° C.

9. The method of claim 8 wherein said temperature is lowered during a time period of about 2 to 12 hours.

10. The method of claim 9 wherein said temperature is gradually lowered over said time period.

11. The method of claim 1 wherein said second solvent is n-Heptane and said first solvent is methylcyclohexane, and further wherein said n-Heptane is added to said moxidectin/methylcyclohexane solution at a ratio of about 3:1 for n-heptane to methylcyclohexane.

12. The method of claim 1 wherein the second solvent is n-hexane and said first solvent is methylcyclohexane, and further wherein said n-hexane is added to said moxidectin/methylcyclohexane solution at a ratio of about 3:1 for n-hexane to methylcyclohexane.

13. The method of claim 1 wherein part b) said solution is concentrated under vacuum.

14. The method of claim 13 wherein part b) said solution is concentrated at a temperature within a range of about 40 to 50° C.

15. The method of claim 14 wherein part b) said solution is concentrated at a temperature within a range of about 45 to 50° C.

16. The method of claim 1 wherein part a) said moxidectin is amorphous moxidectin.

17. The method of claim 16 wherein said moxidectin is obtained from a deblocking chemical reaction.

18. The method of claim 17 wherein said chemical reaction is an alkaline hydrolysis reaction.

19. The method of claim 18 wherein said amorphous moxidectin has a purity of about 90-92%.

20. The method of claim 1 wherein said moxidectin is combined with said first solvent in a weight ratio of about 1:1 to 1:2.

21. A method to purify solid moxidectin, the method comprising:
   a) dissolving solid moxidectin in methylcyclohexane, (MCH), resulting in a moxidectin/MCH solution;
   b) concentrating said moxidectin/MCH solution at a pot temperature of about 45° C. to 50° C. under vacuum;
   c) adding n-heptane to the moxidectin/MCH solution, at a ratio of about 4:1 n-heptane to MCH, under agitation;
   d) aging the resultant solution for about 4-5 hours at about 30° C.;
   e) aging said solution at a temperature of about 10° C. for about 2-3 hours so as to generate moxidectin crystals; and
   f) filtering and drying said crystalline moxidectin under vacuum.

22. The method of claim 21 wherein said crystalline moxidectin is at least about 94-96% pure.

23. A process for generating moxidectin crystals from amorphous moxidectin, which comprises:
   a. adding amorphous moxidectin to a first solvent to produce a moxidectin solution wherein said first solvent is methylcyclohexane, and thereafter
   b. causing the weight percentage of moxidectin within said solution to be within the range of about 40-44% at a temperature within the range of about 45-50° C. for said solution;
   c. cooling said solution and adding a second solvent to said moxidectin solution at a temperature within the range of about 30-35° C. for said solution wherein said second solvent is selected from hexane, heptane, toluene, isooctane or a mixture thereof and is added in a weight ratio of 2:1 to 6:1 of second solvent to first solvent;
   d. lowering the temperature of said solution to about 10° C. over the period of about 2-8 hours, while agitating said solution such that said agitation increases over said period so as to effect crystallization of said moxidectin; and
   e. drying said moxidectin crystals.

24. The process of claim 23 wherein said moxidectin crystals are 2-5% purer than said amorphous moxidectin.

* * * * *